(12) United States Patent
Lin et al.

(10) Patent No.: US 8,907,900 B2
(45) Date of Patent: Dec. 9, 2014

(54) TOUCH-CONTROL MODULE

(75) Inventors: Jao Ching Lin, Taipei (TW); Chung Yi Shen, Taipei (TW); Wen Ting Lee, Taipei (TW); Lin abel Chu, Taipei (TW)

(73) Assignee: Sentelic Corporation, Taipei (TW)

( * ) Notice: Subject to any disclaimer, the term of this patent is extended or adjusted under 35 U.S.C. 154(b) by 554 days.

(21) Appl. No.: 12/418,241

(22) Filed: Apr. 3, 2009

(65) Prior Publication Data

US 2010/0207892 A1  Aug. 19, 2010

(30) Foreign Application Priority Data

Feb. 19, 2009  (TW) .............................. 98202375 U

(51) Int. Cl.
  *G06F 3/041* (2006.01)
  *G06F 3/0488* (2013.01)
  *G06K 9/00* (2006.01)

(52) U.S. Cl.
  CPC ........ *G06F 3/04883* (2013.01); *G06K 9/00429* (2013.01); *G06F 2203/04808* (2013.01)
  USPC ............ 345/173; 345/174; 345/157; 345/160

(58) Field of Classification Search
  None
  See application file for complete search history.

(56) References Cited

U.S. PATENT DOCUMENTS

| | | | |
|---|---|---|---|
| 2002/0015024 A1* | 2/2002 | Westerman et al. | 345/173 |
| 2006/0010400 A1* | 1/2006 | Dehlin et al. | 715/856 |
| 2006/0045345 A1* | 3/2006 | Wu et al. | 382/187 |
| 2008/0036743 A1* | 2/2008 | Westerman et al. | 345/173 |
| 2010/0060586 A1* | 3/2010 | Pisula et al. | 345/169 |

* cited by examiner

*Primary Examiner* — Joseph Haley
*Assistant Examiner* — Ifedayo Iluyomade
(74) *Attorney, Agent, or Firm* — CKC & Partners Co., Ltd.

(57) ABSTRACT

A touch-control module for recognizing gesture inputs by a position sensitive device to an electronic device is disclosed. The touch-control module includes an input connected to the position sensitive device for receiving at least one sensing signal generated by the position sensitive device when one or more objects touch a surface thereof; a touch state unit for detecting the sensing signal and determining a touch state of the object(s), such as approaching to or lifting off the position sensitive device; a position and multi-gesture processing unit for analyzing the sensing signal to determine a touch position of the object(s) on the position sensitive device, and tracking the touch state and touch position to determine a corresponding motion factor; and an output connected to the electronic device for outputting the touch state and touch position as well as information corresponding to a motion factor whenever the motion factor is determined.

9 Claims, 11 Drawing Sheets

| Code | Multi-gesture | Description |
|---|---|---|
| 01 | • | Click |
| 02 | • • | Dbl Click |
| 03 | • → | Drag |
| 04 | ← | Line_W |
| 05 | → | Line_E |
| 06 | • | Dot |
| 07 | ↑ | Line_N |
| 08 | ↖ | Line_NW |
| 09 | ↙ | Line_S_W |
| 10 | ↓ | Line_S |
| 11 | ↘ | Line_SE |
| 12 | ↗ | Line_NE |

Fig.8

| Gesture symbol | Code combination | Gesture event |
|---|---|---|
| ↑ | 05、11、09 | PLAY |
| ✕ | 11、09 | STOP |
| ⋀ | 11、09、10 | NEXT |
| ⋁ | 10、09、11 | PREV |

Fig.9

TOUCH-CONTROL MODULE

FIELD OF THE INVENTION

The present invention relates to a touch-control module, and more particularly to a touch-control module capable of converting at least one sensing signal generated by a position sensitive device into diversified input information.

BACKGROUND OF THE INVENTION

Following the gradually matured techniques for portable electronic products and the reduced part and component cost thereof, various kinds of mobile products, such as cellular phones, personal digital assistants (PDAs), etc., have become very popular among consumers. Nowadays, consumers not only expect these mobile products to provide the so-called basic functions, but also more added functions. Therefore, personal mobile products that provide different added recreational video functions to allow a user to watch television, play movies, listen music, or even browse or edit web pages are most welcomed among consumers.

When a product with various added functions becomes a home or recreational electronic product, the original operations like moving cursor, clicking, or setting hot keys can no longer meet most consumers' expectation in having home or recreational products that can be very conveniently operated. Complicated operating procedures tend to largely reduce consumers' interest in using the products. On the other hand, products with simple, easy and intuitive operating procedures often attract and drive consumers to buy them. Some successful examples of such products include iPod™, iPhone™, etc.

Generally, a portable electronic product has a touch panel to serve as an input interface thereof. When a user moves or taps a finger or an object on the touch panel, usable options can be displayed for the user to click and enter a selected function. However, when the user uses an information or recreational interface that actually requires only very simple operating procedures, the actions of moving cursor and clicking would become relatively complicate to adversely affect the convenience in operation. For example, when a user wants to use MP3 or MP4 music and video playing functions on a walkman, the user would never wish to open a song menu by moving a finger to a specified position and clicking on a desired song. However, with the conventional portable electronic product using a touch panel as an input interface, when the user simply wants to jump to a next song, he or she still has to select the song through the menu.

In a currently frequently adopted way for using the portable electronic product with added information and recreational video functions, a user has to enter a specific mode using a specific gesture or one or more hot keys. For example, the user first uses multiple fingers to touch the touch panel to enter a video mode. After entering the video mode, the original cursor functions of the touch panel are temporarily disabled and replaced by various gesture operations effective in the video mode. For example, draw a circle clockwise would mean "FORWARD", draw a circle counterclockwise would mean "BACKWARD", and draw a cross would mean "STOP". When it is desired to switch to another mode, such as return to the original cursor mode, the user has to make a gesture for exiting the video mode before he or she can enter the target mode, that is, the cursor mode. Through mode switching, the touch panel allows a user to execute different trigger events on a one-to-one basis in different modes with only a few gestures. However, the user has to troublesomely repeat the actions of entering and exiting a mode. And, for each additional mode, an additional gesture determining circuit and an additional one-to-one comparing circuit must be provided. By doing this, a lot of time is wasted in computing and a large space is needed for the complicated circuits, and the electronic device will consume more power and become inconvenient for use.

In U.S. patent application Ser. No. 11/700,636 entitled Gesturing with Multipoint Sensing Device, there is disclosed an electronic system having a position sensitive device B for performing special gesture functions. Please refer to FIG. 1. In the above-described electronic system, cursor functions and gesture functions are implemented in a position calculating module D1 and a gesture recognizing module D2, respectively. Therefore, the electronic system further requires a mode switching module D3 to enable a user to switch the functions between the position calculating module D1 and the gesture recognizing module D2. The user has to make a specific gesture, such as touches with multiple fingers, so as to enable the above-mentioned mode switching function. Then, the user has to make the specific gesture again to trigger and open a gesture set built in the gesture recognizing module D2. Thereafter, the user inputs one of a plurality of gestures preset in the gesture set in order to perform a corresponding gesture event. In the case the function to be performed is not included in the existing gesture set, the user has to exit the gesture set and makes the mode switching gesture again, and then follows the operating procedures for the gesture set in order to perform the desired function.

While the conventional gesture module can interrupt the original cursor input function and trigger specific events with various specific gestures, the user must first complete the mode switching each time to use different functions. That is, the user is not allowed to directly and quickly operate a desired function. Further, the number of modes and the gesture events in each of the modes are predetermined and could not be freely updated or modified with changes in the applied electronic product and the user interfaces thereof. Though it is possible to set the functions of the conventional gesture module in a software program of the applied electronic product to allow convenient update of gesture events, all the complicated circuit lines on the position sensitive device must be connected to the electronic product. This would cause difficulties in arranging the flat cable for the electronic product. Meanwhile, signal distortion and increased noise during signal transmission via circuit lines would also largely increase the difficulty in gesture recognition. Moreover, the electronic product has to undertake the calculation of gesture recognition as well as its own computation load; this will bring to divided computing and form a potential problem in gesture recognition.

If the main function of gesture recognition is allocated to and completed by the hardware of the touch panel, the gesture recognition ability and speed can be entirely ensured, and all the sensing signals thereof are subject to the least interference to maintain the whole position sensitive device at a high sensitivity without the need of providing additional connecting interface or other integrated circuit (IC) modules in the electronic product. And then, if the gesture recognizing results can be automatically combined in the electronic product to initiate an adequate trigger command, the electronic product under the currently used user interface shall be able to select whether to perform the function triggered by the combination. In this manner, a user can directly make a desired gesture on the touch panel without the need of switching to another operating mode. Therefore, it is not necessary for the user to remember various gestures for use in different operating modes or repeat the mode switching to enter or exit a mode.

It is therefore tried by the inventor to develop a touch-control module that has both cursor functions and gesture determining function to enable simplified circuitry and flat cable design, and the gesture determining results thereof can be diversified without being limited to the one-to-one correspondence to gesture events. In this manner, the touch-control module can be used with various customized electronic products and the applied user interfaces thereof, and the user does not need to remember different gestures for different operating modes or repeat mode switching to enter or exit different modes.

SUMMARY OF THE INVENTION

A primary object of the present invention is to provide a touch-control module for recognizing inputs to an electronic device via a position sensitive device.

Another object of the present invention is to provide a touch-control module that can recognize not only the cursor positioning functions, but also motion factors of gestures synchronously.

A further object of the present invention is to provide a touch-control module allowing diversified inputs to the electronic device.

A still further object of the present invention is to provide a touch-control module that has handwriting recognizing function.

To achieve the above and other objects, the touch-control module according to a preferred embodiment of the present invention includes an input connected to the position sensitive device; a touch state unit for detecting at least one sensing signal generated by the position sensitive device when an object touches the same; a position and multi-gesture processing unit; and an output connected to the electronic device. Since a touch state and a touch position of the objects touching the position sensitive device as well as possible gesture-associated commands all can be sent to the electronic device, diversified inputs to the electronic device is enabled.

For the touch-control module of the present invention to synchronously recognize the cursor positioning functions and the motion factors of gestures, the touch state unit detects the sensing signal input to the touch-control module and determines a touch state of the object, such as approaching and lifting of the object to and off the position sensitive device, and the position and multi-gesture processing unit determines touch position of the object on the position sensitive device according to the sensing signal, so as to achieve the cursor positioning functions. Meanwhile, the position and multi-gesture processing unit will keep tracking the touch state and the touch position of the object to generate a corresponding motion factor. Not only the touch state and touch position that provide the cursor positioning functions are output to the electronic device via the output, information corresponding to the motion factor will also be sent to the electronic device as soon as the motion factor is determined. In this manner, both of the cursor-related information and the gesture-related motion factor information can be sent to the electronic device, and the gesture determining function can be directly performed without the need of mode switching.

In the present invention, the motion factor means a basic motion in a gesture, and it can perform a specific gesture through a combination of motion factors. The determination of gesture functionality is left to the electronic device, so that the gesture functions can be diversified and especially for currently used applications or system. Since the complicated motion determination is completed directly in the touch-control module, the electronic device needs only to do simple combination of motion factors to easily recognize a gesture command without occupying the CPU time of the electronic device. Thus, even if the electronic device is replaced with a new one or a user interface thereof is changed, the original touch-control module can still be applied to the new electronic device or the new user interface without circuit modification of the touch-control module due to changes in gestures or functions corresponding thereto.

To enable the handwriting recognizing function, the touch-control module of the present invention can further include a handwriting recognizing unit for determining handwritten words and patterns. The handwriting recognizing unit can also refer to the sensing signal or the motion factor information as a basis in determining the handwritten words or patterns, so as to shorten the time needed to compute and compare during the handwriting determination. Meanwhile, in the present invention, since the handwriting recognizing unit is arranged in the touch-control module in the form of a hardware circuit instead of being arranged in the electronic device in the form of a software program as in the case of prior art, the handwriting recognizing unit can further refer to the more informative original signal to reduce incorrect determination results. Moreover, the hardware circuit allows better computing effect and signal noise processing, and can therefore provide quicker and more accurate handwriting recognizing.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 8 is a table listing some examples of motion factors and codes assigned thereto; and FIG. 9 is a table listing some examples of gesture symbols and code combinations thereof for different gesture events.

DETAILED DESCRIPTION OF THE PREFERRED EMBODIMENTS

Figure 1:
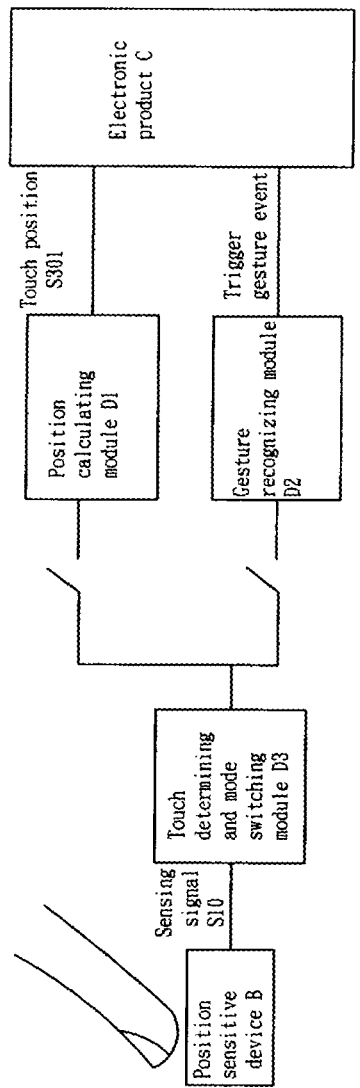
FIG. 1 is a system block diagram of a conventional touch panel technique that requires mode switching.
Figure 2:
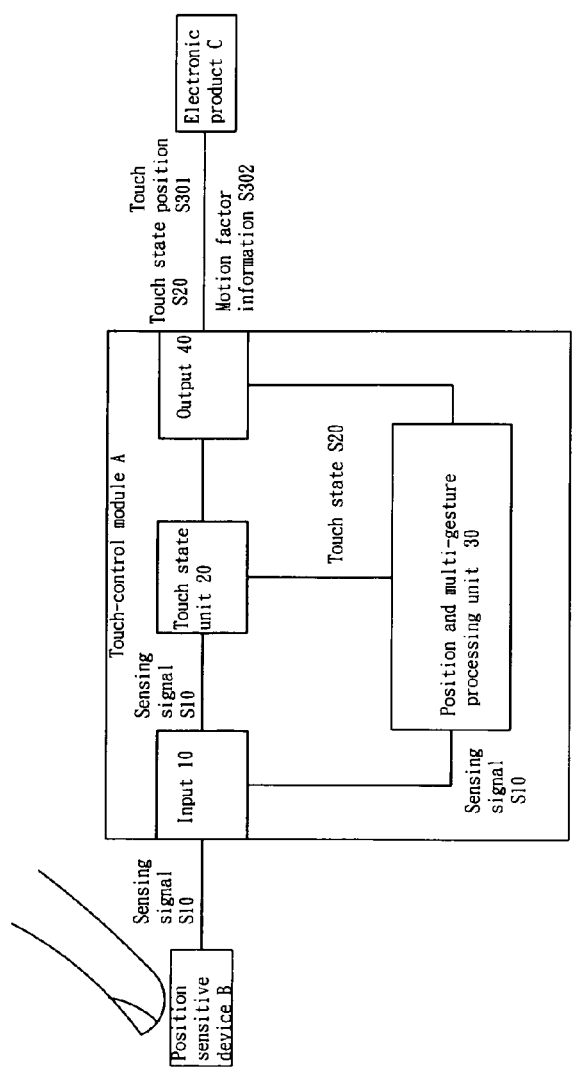
FIG. 2 is a block diagram of a touch-control module according to a preferred embodiment of the present invention.

Please refer to FIG. 2 that is a block diagram of a touch-control module "A" according to a preferred embodiment of the present invention. As shown, the touch-control module A includes an input 10, a touch state unit 20, a position and multi-gesture processing unit 30, and an output 40; and is used to recognize inputs by a position sensitive device "B" to an electronic product "C". The position sensitive device B is capable of sensing touches by one or more objects and outputting at least one sensing signal S10 corresponding to a position at where the object touches the position sensitive device B. In the present invention, since the touch-control module A can directly determine basic motion factors for a gesture without the need of mode switching, it does not require multi-finger gestures for switching between a cursor mode and a specific gesture mode. Therefore, unlike the conventional gesture-trigger technique that requires a multi-object sensing device, such as a capacitive touch panel, the position sensitive device B being used in the present invention can also be other single-object touch sensing devices, such as a resistive touch panel.

As can be seen from FIG. 2, the sensing signal S10 generated by the position sensitive device B is sent to the touch-control module A via the input 10. Then, the touch state unit 20 detects the sensing signal S10 and determines whether there is any object approaching to or lifting off the position sensitive device B, and outputs a corresponding touch state S20. When the touch state unit 20 detects there is an object approaching to or lifting off the position sensitive device B, the position and multi-gesture processing unit 30 will start processing position data provided by the sensing signal S10 to calculate a touch position S301 at where the object touches the position sensitive device B.

In addition to the calculation of the touch position S301 of an object, the position and multi-gesture processing unit 30 also tracks the touch state S20 and the touch position S301. For example, the position and multi-gesture processing unit 30 is also capable of tracking: whether a finger first touches and then lifts off; the time period for the finger touching; the time intervals between two or more successive touches; the number of fingers presented in the same time; the trajectory formed by the moved touch positions; the moving directions of different trajectories; the relative motion between trajectories; the collective motion of trajectories; the relative distance between trajectories; and etc.

After tracking and finding that one basic motion factor of a gesture has been completed via the object on the position sensitive device B, the position and multi-gesture processing unit 30 can generate information S302 related to the basic motion factor. It is not necessary for the position and multi-gesture processing unit 30 to determine a possible gesture only when whole movement of the gesture has been completed. For example, when gesturing with one finger to indicate an arrow symbol "→", the electronic product equipped with a conventional touch-control module would require the following steps to recognize the gesture: (1) using a specific gesture or pushing a key for switching a mode effective to the arrow symbol; (2) waiting until the whole symbol "→" has been completely drawn and then recognizing the arrow symbol as a pattern having been stored in a database built in the touch-control module; and (3) sending a gesture command corresponding to the arrow symbol to a computer for executing a programmed action of the command. However, with the touch-control module A according to the present invention, a code 05 assigned to an eastward motion factor, as exemplified in FIG. 8, can be generated as soon as an eastward path is drawn for the arrow symbol "→". Thereafter, code 11 and code 09 assigned to a southeastward motion factor and a southwestward motion factor, respectively, will be sequentially generated corresponding to a path sliding toward the southeast and a path sliding toward the southwest.

Even during gesture drawing, the touch state S20 and the touch position S301 will still be sent to the electronic product C via the output 40. Meanwhile, whenever there is any motion factor-related information S302 being generated, such as the codes 05, 11, 09, etc. that are assigned to different motion factors, the generated information S302 will also be immediately output via the output 40. Therefore, the touch-control module A of the present invention not only detects the cursor position, but also synchronously detects basic motion factors of potential gestures. That is, with the present invention, specific gestures can be made without the need of performing mode switching first.

In an operable embodiment of the present invention, when the touch state S20, the touch position S301, and the motion factor information S302 have all been output to the electronic product C, the electronic product C can, according to a special sequence of the received motion factors, automatically determine whether there is existing a corresponding gesture. If not, a cursor behavior represented by the touch state S20 and touch position S301 is directly executed. On the other hand, in the event there is a gesture corresponding to the special sequence of motion factors, the electronic product C will execute a command associated with the gesture without the need of first switching to a mode for the specific gesturing.

Again, taking the arrow symbol "→" as an example, the touch-control module A of the present invention, in addition to constantly outputting the touch states S20 and touch positions S301 generated during the arrow symbol's drawing, will continuously track a path formed by these touch positions S301. When the path is recognized as an eastward stroke, an eastward motion factor is determined. At this point, the touch-control module A will output information S302 related to the eastward motion factor, such as the code 05 assigned to the eastward motion factor, to the electronic product C. Similarly, following the paths formed by a southeastward stroke and a southwestward stroke, the code 11 and the code 09 respectively assigned to the southeastward motion factor and the southwestward motion factor will be sequentially output to the electronic product C.

In the event a video playing system of the electronic product C is currently in operation, the electronic product C will combine and determine the motion factor-related information S302, that is, the codes 05, 11 and 09, to initiate a gesture command PLAY, for example, for playing video signals, as exemplified in FIG. 9. Or, in the event a system of the electronic product C that is currently in operation does not accept the gestured arrow symbol "→", the motion factor-related information S302 output to the electronic product C will not be converted into a gesture command. Or, even if the output motion factor-related information S302 is converted into a gesture command, the gesture command would not be accepted by a user interface of the currently operating system of the electronic product C.

With the present invention, the codes 05, 11 and 09 assigned to the motion factors of the same arrow symbol "→" that is gestured under another different user interface will be interpreted as another different gesture command. For instance, a code combination of the codes 05, 11 and 09 can be recognized as a command PLAY under a video playing system, a command NEXT PAGE under an Internet browsing system, or a command REPEAT under a word editing system. Therefore, the present invention is very convenient for use because a user does not need to switch among different modes in response to different graphics user interfaces (GUI) for entering into different gesture functions or to remember complicated changes in gestures for different operating modes.

With these arrangements, even if the electronic product C is replaced with a new one or the user interfaces built in the electronic product C are changed, the touch-control module A of the present invention can still be applied to the new electronic product C or the new user interfaces without the need of changing the touch-control module A. So long as the user's gestures made on the position sensitive device B can be structurally analyzed with the motion factors stored in the touch-control module A, the electronic product C can always determine the gesture based on a combination of motion factors forming the gesture. It is not necessary for the user to change the circuitry of the touch-control module A. Therefore, the touch-control module A of the present invention has high applicability to be particularly advantageous in the competing market of various mass-produced industrial products. Moreover, the gesture determining circuits for the touch-control module A would not increase with the increase of user interfaces applied in the electronic product C, and the size of the touch-control module A would not change, either. Therefore, the present invention can be used with variety of electronic products.

FIG. 8 is a table listing some examples of motion factors and codes assigned thereto; and FIG. 9 is a table listing some examples of gesture symbols and code combinations thereof for different gesture events (commands). However, it is understood the motion factors and the combinations thereof for determining gestures as adopted in the present invention are not limited to those linear motions listed in the tables of FIGS. 8 and 9. Different motion factors can also be generated when other non-linear patterns, such as a circle, various non-closed curves and spirals, or other specific characters and symbols, are drawn with a touch object.

Figure 5A:
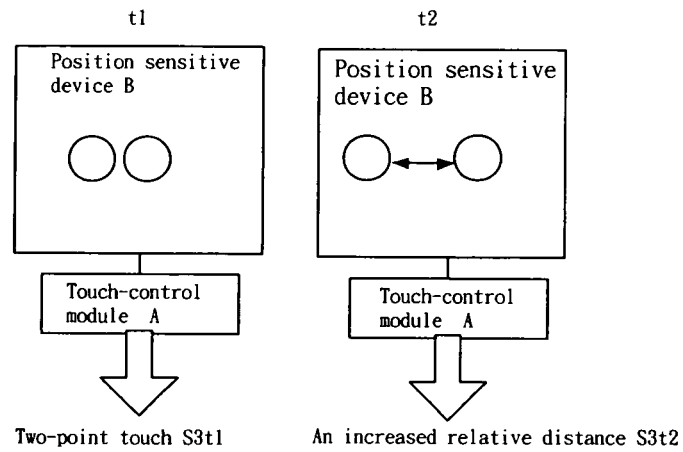
FIG. 5A shows a first example of combining different motion factors.
Figure 5B:
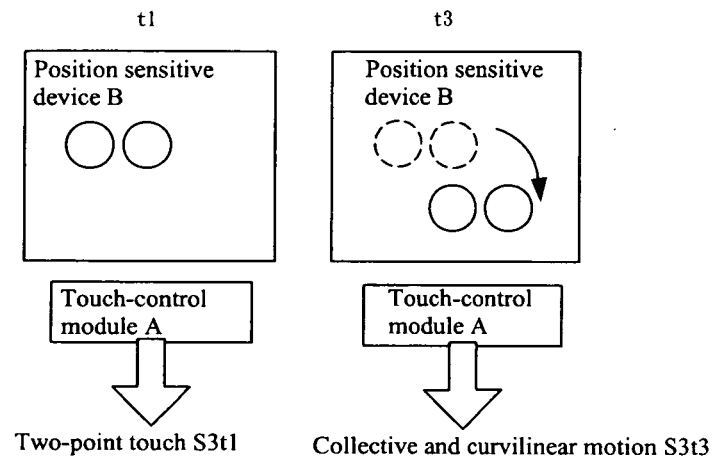
FIG. 5B shows a second example of combining different motion factors.

In addition, the number of fingers being frequently used, the relative motion between or among these fingers, and the collective motion of these fingers can also trigger the generation of different motion factors, as shown in FIGS. 5A and 5B. For example, when two or more fingers are approaching to the position sensitive device B, the fingers can simultaneously touch the position sensitive device B, or sequentially touch the position sensitive device B with the time periods of touch partially overlapped with one another. In either case, the touch-control module A will output a motion factor S3$t$1 indicating a multi-point touch.

Again, information related to the motion factor S3$t$1 does not necessarily bring the electronic product C to act. The electronic product C can automatically determine whether to act in response to the information related to the motion factor S3$t$1.

Or, for example, in a touch state t1 that two or more fingers occur on the position sensitive device B at the same time, as shown at the left side of FIG. 5A, the touch-control module A will first send out the information of motion factor S3$t$1 indicating multi-point touch. And then, the fingers might move relative to one another, such as turn relative to one another, move toward one another, or move away from one another. In a touch state t2 that the fingers move away from one another, as shown at the right side of FIG. 5A, the touch-control module A will further responsively output the information related to a motion factor S3$t$2 indicating an increased relative distance between two touch positions as a result of a relative motion between the fingers. When receiving the information related to the motion factors S3$t$1 and S3$t$2 indicating two relatively separating fingers, the electronic product C can combine the motion factors to initiate a corresponding gesture event or command. In the present invention, the electronic product C can also obtain a span between two separated fingers from the touch positions S301 constantly output thereto.

On the other hand, the objects might move collectively, as shown in FIG. 5B. For example, in the touch state t1 that two fingers occur on the position sensitive device B at the same time, as shown at the left side of FIG. 5B, the touch-control module A will first send out the information of motion factor S3$t$1. And then, a touch state t3 occurs showing the two fingers move collectively, as shown at the right side of FIG. 5B, the touch-control module A will further responsively output information related to a motion factor S3$t$3 indicating a collective and curvilinear motion of the two fingers. After receiving the motion factors S3$t$1 and S3$t$3, the electronic product C can combine them to initiate another specific gesture function.

Figure 6A:
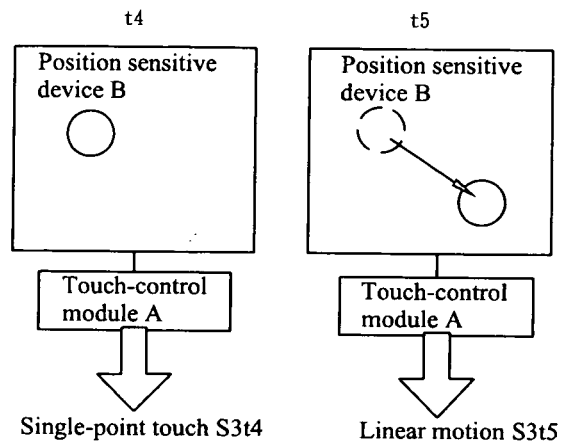
FIG. 6A shows a third example of combining different motion factors.

In addition to the number and position of touch objects, the generation of motion factors can also be triggered by the holding periods of the touch objects, the time period between the approaching and the lifting of the touch object to and off, and the time interval between two touches. Take the holding period of a touch object as an example. In a touch state t4 that an object touches the position sensitive device B as shown at the left side of FIG. 6A, when the touch-control module A detects the touch position has been unchanged for a time period longer than a preset length of time, information related to a motion factor S3$t$4 indicating a stationary single point is output. At this point, the electronic product C can initiate a specific gesture command simply based on the motion factor S3$t$4, or wait for other subsequent motion factors before determining the gesture command to be executed. In the event a touch state t5 occurs, in which the object moves in a linear motion as shown at the right side of FIG. 6A, and the electronic product C further receives within a predetermined time period the information related to a motion factor S3$t$5 indicating a linear motion of the touch object, the electronic product C can combine the information related to the two motion factors S3$t$4 and S3$t$5 to initiate a specific gesture event or command, such as SCROLL or DRAG, that involves in direction and distance.

Figure 6B:
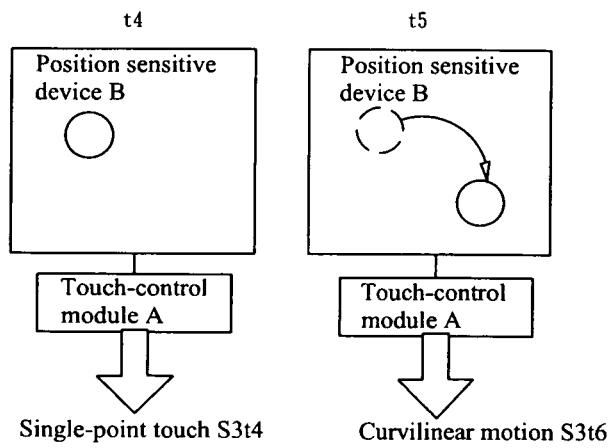
FIG. 6B shows a fourth example of combining different motion factors.

With the same principle, in a touch state t6, the stationary single point can be otherwise moved in a curvilinear motion, as shown at the right side of FIG. 6B. A combination of the motion factor S3$t$4 indicating the stationary single point and another motion factor S3$t$6 indicating a curvilinear motion of the single point can initiate another specific gesture event or command that involves in direction and distance.

The above-mentioned curvilinear motion can also trigger the generation of motion factors separately indicating linear motions in eight different axes, as separately represented by codes 04, 05, 07, 08, 09, 10, 11 and 12 shown in FIG. 8. When the electronic product C first receives the information of motion factor S3$t$4 indicating a stationary single point and then information of another motion factor indicating one of the eight linear motions in different axes and the linear motion changes its angular direction slowly, it can be determined the user wants to scroll the window or drag an object in a fixed direction. And, the amount of scrolling or dragging can also be determined from, for example, number of times the linear motion factor is generated. When the angular direction of the linear motion factor in one of the eight axes is quickly turned reversely, it can be determined the user wants to scroll the window or drag the object in another direction.

In addition to the motion factor corresponding to different touch states and gestures, there are also motion factors generated from the tendency of various dynamic changes in gestures, such as the tendency of increasing or decreasing number of the touch objects, the tendency of moving speed of the touch object, the tendency of moving direction of the touch object, changes in the number of times the touch object touches and then leaves the position sensitive device B, and changes in time duration the touch object touches the position sensitive device B, etc. Of course, as it is often seen, the positions at where the touch object initially touches and eventually leaves the position sensitive device B can also be used to generate the motion factors, for example, for selecting key functions.

Take the number of clicks as an example. A combination of the motion factors codes 05, 11 and 09 indicating different moving directions together with N clicks can trigger the action of, for example, forward skipping N songs; a rightward curve together with N clicks can trigger the action of, for example, forward skipping N screens or browsing N web pages; parting or approaching two fingers from or to each other can trigger, for example, adjustment in size; simultaneous movement of multiple fingers can trigger, for example, a specific gesture event, etc. Therefore, more changeful functions can be triggered using gestures in a more intuitive manner.

Figure 7:
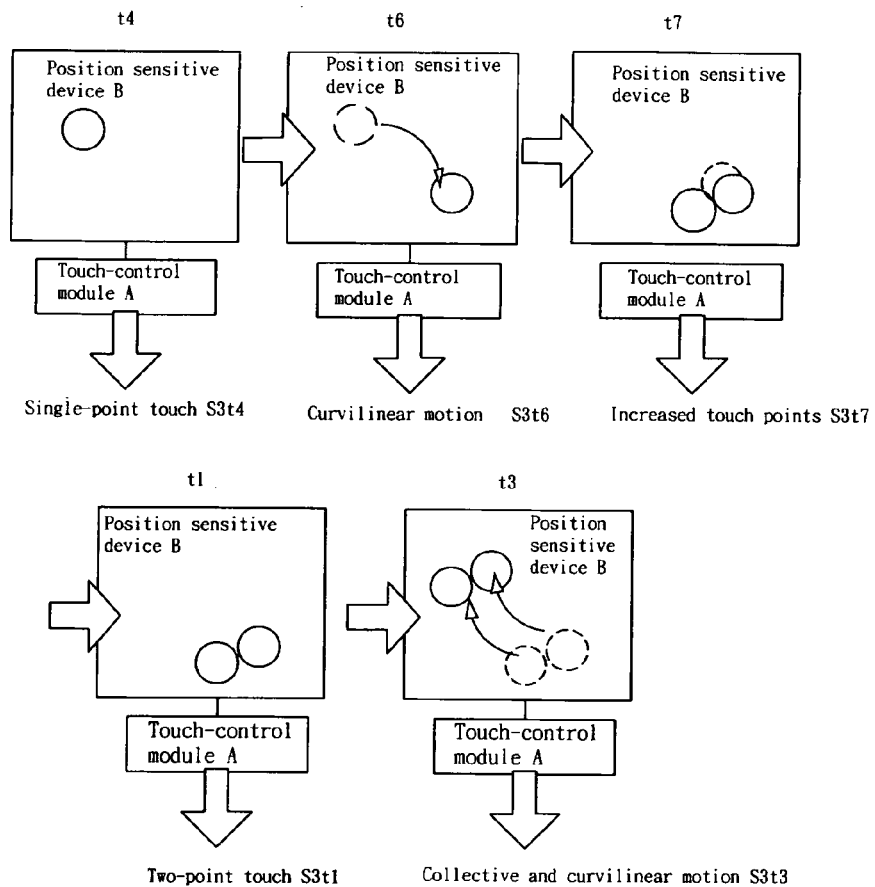
FIG. 7 shows a fifth example of combining different motion factors.

Please refer to FIG. 7 that shows a further example of gesturing on the position sensitive device B. First, touch the position sensitive device B with one finger and wait for a while (that is, touch state t4 and motion factor S3t4 indicating stationary single point) before sliding the finger in a curve (that is, touch state t6 and motion factor S3t6 indicating a curvilinear motion), and then, add on another finger (touch state t7 and motion factor S347) and continue the sliding motion. The electronic product C can combine the first two motion factors S3t4 and S3t6 to initiate a specific gesture event or command. After the number of fingers is increased (touch state t7), the electronic product C will further combine the motion factor S3t7 with the first two motion factors, bringing the previously initiated specific gesture event or command to change to another function or adjust its parameter, such as increase the scrolling speed. Then, the electronic product C accepts a following gesture formed by combining motion factors S3t1 (two touch points) and S3t3 (collective and curvilinear motion).

To allow the user to regret or re-input, the electronic product C can erase previous motion factor combination or occurrence sequence whenever another specific motion factor combination is detected, so that the user can make gesture again or terminate the gesturing.

Moreover, when a single motion factor or a combination of motion factors satisfies some specific conditions or sequence, such as various GUI input actions, including some frequently used commands input via a mouse, such as, single click on left key of a mouse, double click on left key of a mouse, dragging, scrolling up, scrolling down, etc., the position and multi-gesture processing unit 30 can also directly output a corresponding action command to the electronic device via the output 40, so that the user can conveniently use an electronic product having a GUI system without the need of recognizing the motion factor combinations in the electronic product.

Figure 3:
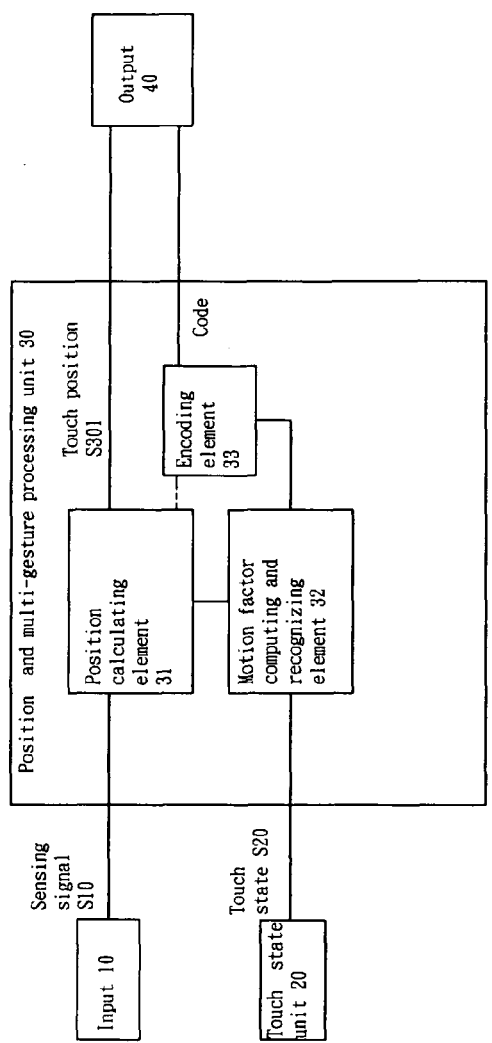
FIG. 3 is a block diagram of an embodiment of a position and multi-gesture processing unit included in the touch-control module of the present invention.

Please refer to FIG. 3. In an embodiment of the position and multi-gesture processing unit 30, there are included a position calculating element 31, a motion factor computing and recognizing element 32, and an encoding element 33. The motion factor computing and recognizing element 32 generates motion factors, which are then encoded by the encoding element 33, so that complicated motion forms can be sent in simple and digitally encoded signals, and the encoded signals allow the electronic device to more easily recognize and combine the motion factors. For example, in the present invention, symbol "→" includes three motion factors, which can be separately encoded to be codes 05, 11 and 09, as shown in FIG. 8. Therefore, it is not necessary to transmit the arrow symbol in complicated graphic signals. Moreover, the digitally encoded signals can be advantageously transmitted via electronic circuit lines without the risk of distortion, and are helpful in subsequent conversion of code combinations into commands.

Figure 4:
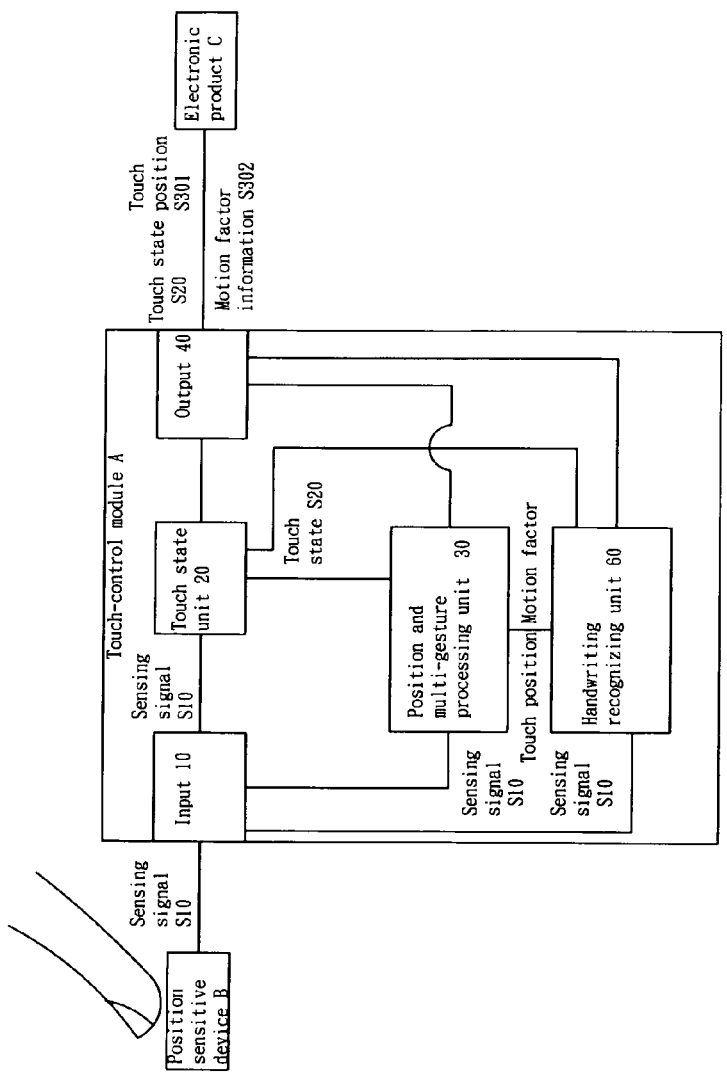
FIG. 4 is a block diagram of a touch-control module according to a second embodiment of the present invention, into which a handwriting recognition function is incorporated.

FIG. 4 is a block diagram of a touch-control module A according to a second embodiment of the present invention. As shown, in the second embodiment, the touch-control module A further includes a handwriting recognition unit 60, in addition to the input 10, the touch state unit 20, the position and multi-gesture processing unit 30, and the output 40. The handwriting recognition unit 60 can track the touch state and the touch position to determine words, numbers, and patterns being manually written or drawn with the touch object on the position sensitive device B. Besides, the handwriting recognition unit 60 can also enhance the handwriting recognition ability by referring to the sensing signal S10 that provides more handwriting-related information, or shorten the time needed for handwriting recognition by referring to different motion factor combinations.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A touch-control module connected to a position sensitive device and an electronic device, comprising:
    an input connected to the position sensitive device for receiving at least one sensing signal generated by the position sensitive device when one or more objects are in the proximity of a surface of the position sensitive device;
    a touch state unit configured to detect the sensing signal and determine touch state of the one or more objects, including approaching to or lifting off the position sensitive device;
    a handwriting recognizing unit configured to track the touch state and the touch position for determining patterns manually written on the position sensitive device by the one or more objects;
    a position and multi-gesture processing unit configured to analyze the sensing signal for determining touch position of the one or more objects associating to the position sensitive device, and to track the touch state and the touch position of the one or more objects for determining a corresponding motion factor, the position and multi-gesture processing unit comprising a position calculating element, a motion factor computing and recognizing element, and an encoding element, wherein a gesture comprises a sequence of multiple motion factors, the encoding element converts each motion factor of the gesture into a predefined unique code in order to produce a sequence of a plurality of unique codes corresponding to a gesture, and the electronic device reads the sequence of the plurality of unique codes for causing the electronic device to perform an action corresponding to the multiple motion factors of the gesture; and
    an output connected to the electronic device for outputting the touch state and the touch position, and also information corresponding to the motion factor whenever the motion factor is determined, to the electronic device for causing the electronic device to perform an action.

2. The touch-control module as claimed in claim 1, wherein, the position and multi-gesture processing unit also tracks the touch state and the touch position occurring time.

3. The touch-control module as claimed in claim 1, wherein, if the number of objects on the position sensitive device is two or more, the position and multi-gesture processing unit can track the touch state and touch position of each of the objects one by one.

4. The touch-control module as claimed in claim 3, wherein the position and multi-gesture processing unit can track relative positions among the objects.

5. The touch-control module as claimed in claim 3, wherein the position and multi-gesture processing unit can track relative speed and moving direction among the objects.

6. The touch-control module as claimed in claim 2, wherein the position and multi-gesture processing unit can track a first change tendency of the touch position within a first time period.

7. The touch-control module as claimed in claim 6, wherein the position and multi-gesture processing unit can further track a second change tendency of the first change tendency within a second time period.

8. The touch-control module as claimed in claim 1, wherein the handwriting recognizing unit refers to the sensing signal in recognizing the patterns.

9. The touch-control module as claimed in claim 1, wherein the handwriting recognizing unit also tracks the motion factors for determining the patterns manually written on the position sensitive device by the one or more objects.

* * * * *